(12) United States Patent
Switzer et al.

(10) Patent No.: US 6,566,102 B1
(45) Date of Patent: May 20, 2003

(54) METHODS AND DEVICES FOR DETECTION OF XENOGENEIC GRAFT PERSISTENCE AND INFECTIOUS AGENTS

(75) Inventors: William M. Switzer, Stone Mountain, GA (US); Walid Heneine, Atlanta, GA (US); Shanmugam Vedapuri, Duluth, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/743,954

(22) PCT Filed: Jul. 16, 1999

(86) PCT No.: PCT/US99/16201

§ 371 (c)(1),
(2), (4) Date: Jan. 12, 2001

(87) PCT Pub. No.: WO00/04191

PCT Pub. Date: Jan. 27, 2000

Related U.S. Application Data

(60) Provisional application No. 60/093,202, filed on Jul. 17, 1998, and provisional application No. 60/098,262, filed on Aug. 28, 1998.

(51) Int. Cl.[7] ............ C12P 19/34; C12Q 1/68; C12Q 1/70
(52) U.S. Cl. ............ 435/91.2; 435/5; 435/6; 536/24.3; 536/24.31; 536/24.33; 536/24.32; 536/23.1
(58) Field of Search ............ 435/6, 5, 91.2; 536/24.3, 24.31, 24.33, 24.32, 23.1

(56) References Cited

U.S. PATENT DOCUMENTS 5,097,024 A    3/1992  Hodes et al.
5,716,787 A    2/1998  Dunn et al.

FOREIGN PATENT DOCUMENTS

| WO | WO 94/21799 | 9/1994 |
|----|-------------|--------|
| WO | WO 9721836  | 6/1997 |
| WO | WO 9740167  | 10/1997 |

OTHER PUBLICATIONS

Mammalian Mitochondrial DNA Evolution: A Comparison of the Cytochrome b and Cytochrome c Oxidase II Genes Honeycutt et. al. J. Mol. Evol (1995) 40: 260–272.*
Michaels et al., *J. Infect. Dis.*, 176:1476–83, 1997.
Heneine & Switzer, *Transplantation*, 62(9):1360–1362, 1996.
Patience et al., *Nature Medicine*, 3(3):282–286, 1997.
Stoye et al., *Nature Medicine*, 1(11):1100, 1995.
Switzer et al., *Transplantation*, 68(2):183–188, 1999.
Wilson et al., *J. Virology*, 72(4):3082–3087, 1998.

\* cited by examiner

*Primary Examiner*—W. Gary Jones
*Assistant Examiner*—Juliet Einsmann
(74) *Attorney, Agent, or Firm*—Klarquist Sparkman, LLP

(57) ABSTRACT

Compositions, methods and diagnostic devices for monitoring graft integrity in xenotransplantation and for detecting infectious agents transmitted by the xenograft are described. In particular, the compositions, methods and devices are useful for determining porcine xenograft integrity and persistence and can detect the presence of PERV (porcine endogenous retrovirus) in a biological sample. The compositions, methods and devices are useful for determining or monitoring graft survival and rejection in recipients of xenografts and are useful for detecting the presence of pig cell and PERV infection in a xenotransplant recipient or donor. In addition, the compositions, methods and devices are useful for screening therapeutic products to be administered to humans to ensure that the products are free of pig cells, and thus free of PERV contamination, prior to administration.

23 Claims, 7 Drawing Sheets

Figure 2A
Figure 2B
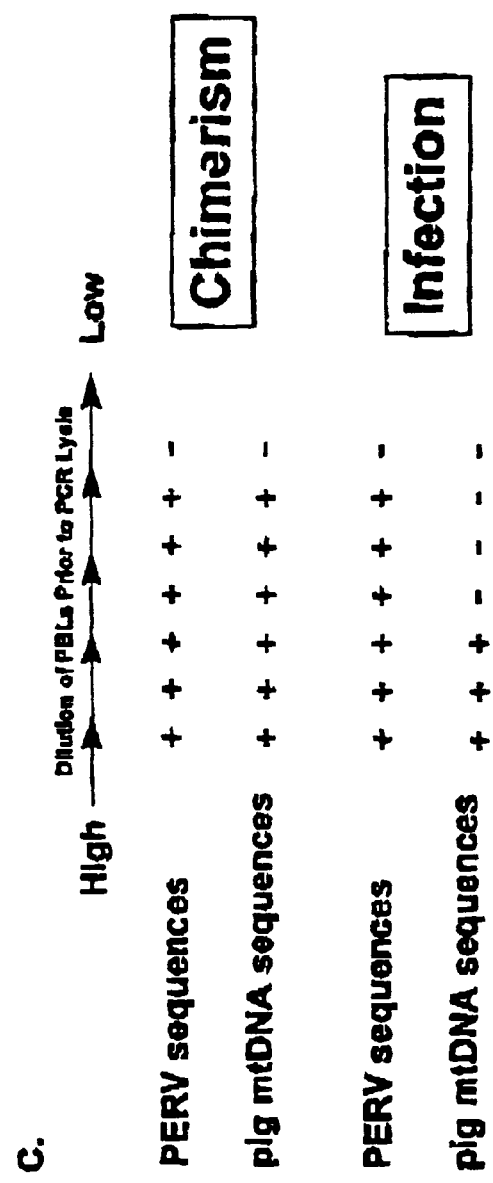
Figure 2C
Figure 2

METHODS AND DEVICES FOR DETECTION OF XENOGENEIC GRAFT PERSISTENCE AND INFECTIOUS AGENTS

This appln is a 371 of PCT/US99/16201 filed Jul. 16, 1999 which claims benefit of Prov. No. 60/093,202 filed Jul. 17, 1998 which claim benefit of Prov. No. 60/098,262 filed Aug. 28, 1998.

This invention was made by the Centers for Disease Control and Prevention, an agency of the United States Government.

TECHNICAL FIELD

The present invention relates to compositions, methods and devices for the detection of infections resulting from xenogeneic transplants, particularly those caused by endogenous retroviruses. In particular, the present invention comprises compositions, devices and methods for the detection of porcine transplant materials, detection of which is necessary following xenotransplantation of porcine cellular products.

BACKGROUND OF THE INVENTION

Currently, there are shortages of human organs, tissues and cells for transplantation into humans. Many patients awaiting a transplant die due to the lack of donor material. These shortages of human donor material suitable for allotransplantation, coupled with recent advances in transplantation immunology, have provided impetus for attempts to develop xenotransplantation—the therapeutic use of living animal tissues and organs in humans.

Although xenotransplants from animals such as pigs, baboons, and cows offer an unlimited source of organs and tissues, the therapeutic promise of xenotransplantation has not yet become widely accepted. The transplantation of simian organs and porcine cells and organs into humans has been reported, and progress has been encouraging enough to merit the beginning of limited clinical trials in the United States.

Pigs are among the primary animal species proposed as sources of xenografts. Xenotransplantation clinical trials involving porcine tissue being considered or underway include the perfusion through or implantation of whole liver preparations as a treatment for hepatic failure, the implantation of fetal neuronal tissue as a therapy for Parkinson's disease, and the infusion or implantation of pancreatic islet cells as a treatment for diabetes mellitus. However, after xenotransplantation, detection and determination of persistence of the graft often involves expensive tests, such as CT scans, or invasive procedures such as a biopsy of the graft. When the graft is a diffuse transplantation of cells, sometimes none of these techniques are effective. What is needed are simple, non-invasive techniques for monitoring the presence and condition of the xenotransplantation materials.

In addition, concerns have been raised that the implantation of porcine tissue and/or cells into immune compromised humans may facilitate the transmission of new infectious agents to humans. The Public Health Service has therefore stressed the importance of proceeding with xenotransplantation clinical trials only after appropriate monitoring tests are available. What is especially needed are diagnostic tools that can determine the difference between transplanted xenograft materials and infectious agents that may originate from and may be present in the same xenotransplanted materials. Surveillance programs for new xenograft recipients need to be developed, and persons exposed to xenografts can be tested for evidence of graft persistence and possible xenogeneic infection.

Porcine tissues and cells are known to be infected with endogenous retroviruses. The genomes of all domesticated swine species tested thus far contain multiple integrated copies of an endogenous C-type retrovirus termed porcine endogenous retrovirus (PERV). The risks of transmission of known infectious agents may be reduced, or eliminated by procuring source animals from specific pathogen-free colonies. Therefore, one method for stopping the transmission of porcine endogenous viruses from xenotransplantation would be to harvest the transplantation materials from virus-free animals. However, this pre-transplant screening method cannot eliminate the porcine endogenous retrovirus (PERV), because the genome of these viruses is carried in the germ line of every pig. Pig PERV particles of type C morphology are released spontaneously by cell lines originating from a variety of pig tissues including kidneys, lymph nodes, testes and fallopian tubes. All known PERVs originate from healthy porcine tissues except for two known types, PERV-Shimozuma-1 and 38A-1 which are derived from porcine lymphomas.

The knowledge that PERV originating from both porcine cell lines and primary porcine lymphocytes can infect human cells in vitro has heightened safety concerns related to pig xenografts. Transmission of xenogeneic retroviral infections to xenograft recipients is of particular concern because retroviruses are known to result in life long persistent infections. Risks for xenogeneic infections may be significantly increased by the immunosuppressive therapies required to maintain graft function in human xenotransplant recipients. Currently, there are no rapid, inexpensive, and relatively noninvasive tests that can determine the presence of a xenotransplant and that may also determine that the patient is also free of a potential virus transmitted by the transplant. The current absence of the ability to detect the presence of PERV, which hampers the determination of whether PERV will infect humans exposed to porcine xenografts, and whether PERV will be transmitted secondarily among their contacts, has raised questions on the safety of pig-to-human transplantation, and threatens to delay progress in this therapeutic technology.

Accordingly, there is a need for rapid, sensitive, and specific compositions, methods and devices for detecting the presence and persistence of a xenotransplant in a xenotransplantation recipient and the status of xenograft survival. Further, there is a need to be able to determine the presence of any viruses or other infectious agents that might be present in the xenotransplant material, or transplant donor or the xenotransplant recipient. Additionally, there is a need to be able to determine graft status using noninvasive techniques, such as using body fluids from the transplant recipient. Such compositions, methods and devices would be particularly important for providing diagnostic and physiologic information for patients receiving porcine xenotransplants.

SUMMARY OF THE INVENTION

The present invention provides compositions, methods and devices for determining and monitoring xenograft integrity. The compositions, methods and devices are useful for determining or monitoring graft survival and rejection in recipients of xenografts. In addition the compositions, methods and devices are useful for differentiating between the presence of xenotransplant donor cells and the presence of xenogeneic endogenous retrovirus infections in a xenograft recipient. In particular, the compositions, methods and devices are useful for the differentiation between porcine cell microchimerism and true xenogeneic infection. Furthermore, the compositions, methods and devices are highly sensitive and can detect very low copy numbers of porcine or endogenous porcine viral sequences in the presence of 1 μg of human DNA. The compositions, methods and devices are useful in defining the risks associated with the use of xenotransplantation, and in particular, porcine xenotransplantation. A particular advantage of the present invention is that body fluids of the transplant recipient can be used with the compositions, methods and devices of the present invention in determining the presence and persistence of the xenotransplant.

The compositions described herein comprise nucleic acid probes and primers useful for the amplification and detection of donor cells, such as probes for porcine mitochondrial DNA (mtDNA) and RNA, and for the presence of endogenous retroviruses. The methods described herein utilize the probes and primers with known amplification and detection techniques. The devices described herein employ the compositions and various components of the methods to facilitate the detection of the transplant and any endogenous virus. For example, the devices can be used to detect porcine cells, particularly porcine mtDNA and RNA, and PERV sequences.

Accordingly, it is an object of the present invention to provide methods and compositions for the rapid, sensitive, and specific detection of xenogeneic nucleic acids in body fluids and tissues of xenograft recipients.

Another object of the present invention is to provide compositions, methods and devices for monitoring xenograft survival and rejection.

Yet another object of the present invention is to provide compositions, methods and devices for differentiating between the presence of animal donor cells and infections such as those with endogenous retroviruses.

Another object of the present invention is to provide compositions, methods and devices that employ biological fluids such as serum or plasma for use in biological assays.

Still another object of the present invention is to provide compositions, methods and devices for screening for infectious agents inherently present in pig xenografts, by detecting pig cell-specific markers in biological products such as pig factor VIII, porcine insulin and porcine heparin.

It is another object of the present invention to provide compositions, methods and devices for detecting the presence of endogenous retroviruses in transplant material, including tissues, organs and cells.

Still another object of the present invention is to provide compositions, methods and devices for determining the zoonotic potential and tissue tropism of endogenous retroviruses.

These and other objects, features and advantages of the present invention will become apparent after a review of the following detailed description of the disclosed embodiments and the appended claims.

BRIEF DESCRIPTION OF THE DRAWINGS

FIG. 2 shows limiting dilution PCR analysis which was used to distinguish true xenogeneic infection with porcine endogenous virus (PERV) from xenograft microchimerism in PERV-positive samples. Panel A. PCR detection of PERV gag sequences in PERV-infected human 293 cells spiked with a single pig PBL or pig PBLs alone followed by end point titration to a single cell. Panel B. PCR detection of pig mitochondrial DNA (mtDNA) sequences in the same samples. Lanes 1 to 7 and lanes 8 to 14 are representative results from ten fold serial dilutions of 100,000 to 0 PERV-infected 293 cells and pig PBLs, respectively; lanes 15 and 16, negative DNA lysate controls; lane 17, water negative control; lane 18, positive DNA control from porcine PK15 cell lysates representing DNA equivalents of 0.15 or 0.015 cells for the PERV gag and pig mtDNA assays, respectively. Panel C. Diagram depicting interpretation of PERV gag and pig mtDNA PCR results.

DETAILED DESCRIPTION

Figure 1:
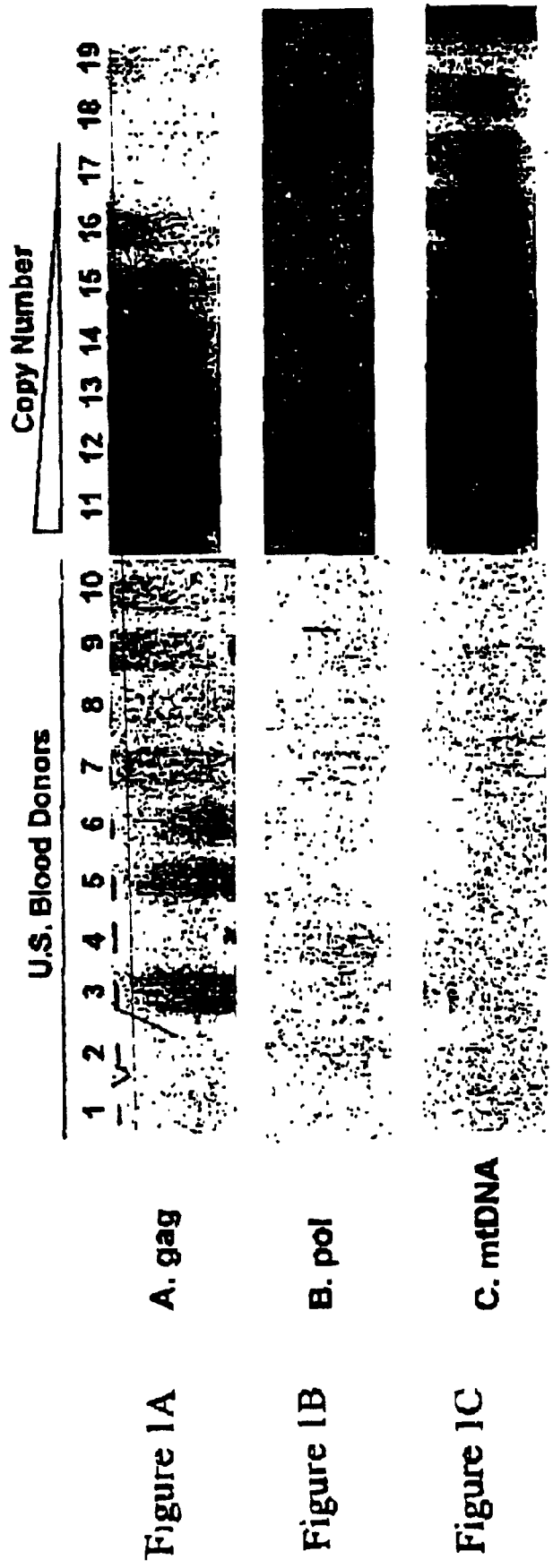
FIG. 1 is a PCR analysis that shows the specificity and sensitivity analysis of porcine endogenous virus (PERV) and pig mitochondrial (mtDNA) PCR assays. Panel A. PERV gag PCR; Panel B. PERV polymerase PCR; Panel C. Pig mtDNA PCR. Lanes 1 through 10 are DNA lysates from 10 randomly selected, U.S. blood donors. Lanes 11 to 17 are dilutions of PERV gag and pol, and pig mtDNA target sequences from 10,000 to 0.1 copy in 1 μg of human DNA lysate, respectively. Lanes 18 and 19 are 1 μg human DNA lysate alone and water, respectively.

Compositions and methods for detecting and monitoring xenograft survival and infectious agent presence in a biological sample from a xenograft recipient are provided. Diagnostic devices employing these compositions and methods are also provided. The compositions, methods and devices are useful for determining or monitoring graft survival and rejection in recipients of xenografts. In addition the compositions, methods and devices are useful for differentiating between the presence of xenogeneic donor cells and xenogeneic endogenous retrovirus infections in a xenograft recipient. Furthermore, the compositions, methods and devices use noninvasive methods for monitoring graft presence and persistence. Body fluids of the xenograft recipient can be easily obtained and used in the biological detection assays described herein. The present invention can be used for screening therapeutic products to be administered to humans to ensure that the products are free of donor animal cells and thus free of infectious agent contamination prior to administration to the human.

Definitions

The terms "a", "an" and "the" as used herein are defined to mean one or more and include the plural unless the context is inappropriate.

The terms "nucleic acid" or "nucleic acid molecule", as used. herein, refer to a deoxyribonucleotide (DNA) or ribonucleotide (RNA) in either single- or double-stranded form, and unless otherwise limited, encompass known analogs of natural nucleotides which can function in a manner similar to the naturally occurring nucleotides.

Detection of Porcine mtDNA

The compositions, methods and devices described herein for monitoring porcine graft survival, which indicates that the graft is present and has not been rejected, are nucleic acid probes and primers useful in methods for the amplification and detection of porcine mitochondrial DNA (mtDNA) in a biological sample taken from the xenograft recipient. The methods described herein utilize the novel probes and primers of the present invention with known amplification and detection techniques. The devices described herein employ the compositions and various components of the methods to facilitate the detection of the porcine mtDNA.

The nucleic acid primers and probes are used to amplify and detect a 255 basepair sequence from the porcine cytochrome oxidase subunit II (COII) gene.

A first preferred primer is the primer PMTF2, which is a nucleic acid having the sequence of SEQ ID NO:1, which is as follows:

5' TCA CCC ATC ATA GAA GAA CTC CTA CA 3'

A second preferred primer is the primer PMTR2, which is a nucleic acid having the sequence of SEQ ID NO:2, which is as follows:

5' TTT TAC GGT TAA GGC TGG GTT ATT AAT T 3'

Preferably, the primers PMTF2 and PMTR2 are used as a primer pair to amplify the 255 basepair sequence from the porcine COII gene by a nucleic acid amplification method such as the polymerase chain reaction.

A first preferred probe is the probe PMTP1, which is a nucleic acid having. the sequence of SEQ ID NO:3, which is as follows:

5' GAC ACA CAC TAG CAC AAT GGA TGC 3'

The probe is used for detection of the amplified product. Any probe capable of detecting the amplified product can be used with the present invention.

PERV sequences are present in all pig cells and thus, microchimerism can result in a positive result in a PERV PCR assay in a xenograft recipient. This result would complicate the interpretation of the PERV infection status of such a xenograft recipient. The compositions, methods and devices of the present invention can be used to distinguish between the presence of pig donor cells containing PERV sequences and a true xenogeneic PERV infection by detecting pig-specific mtDNA sequences in clinical samples from xenograft recipients.

In accordance with the methods for detecting and monitoring the integrity or survival of a xenograft, a primer pair specific for porcine mtDNA, preferably the pair disclosed above, is incubated with a biological sample taken from the xenograft recipient and reacted in amplification conditions for a sufficient amount of time for the amplification of porcine mtDNA. The amplified porcine mtDNA is then detected with a probe, preferably the probe described above, which has been labeled with a detectable label in accordance with methods well known to those skilled in the art. Detection of the label indicates the presence of porcine mtDNA in the sample, which is evidence that the xenograft may have survived. The failure to detect label indicates the absence of porcine mtDNA in the sample, suggesting that the xenograft was unsuccessful or rejected.

Detection of PERV RNA and DNA

The compositions described herein for the detection of PERV are nucleic acid probes and primers useful in methods for the amplification and detection of PERV RNA in a biological sample. The biological sample is taken from a xenograft donor or a xenograft recipient. The methods described herein utilize the probes and primers with known amplification and detection techniques. The devices described herein employ the compositions and various components of the methods to facilitate the detection of PERV RNA.

The nucleic acid primers and probes are conserved PERV sequences identified from an alignment of all known PERV variant sequences. Wobble bases and inosines (I) are used to accommodate nucleotide variability at certain positions in these oligonucleotides.

A first preferred primer is the primer PK15GF2, which is a nucleic acid having the sequence of SEQ ID NO:4, which is as follows:

5' CCA CAG GGC AAC (G/A)(G/A)C AGT ATC CAT G 3'

A second preferred primer is the primer PK15GR2, which is a nucleic acid having the sequence of SEQ ID NO:5, which is as follows:

5' TTG GAG GGT CAA CAC AGT GAT IGG 3'

Preferably, the primers PK15GF2 and PK15GR2 are used as a primer pair to amplify a 212 basepair sequence of the PERV polymerase gene by a nucleic acid amplification method such as the polymerase chain reaction.

A third preferred primer is the primer PRETF1, which is a nucleic acid having the sequence of SEQ ID NO:6, which is as follows:

5' CGG CAA GAG AAG AAT TTG ACT AAG ATC 3'

A fourth preferred primer is the primer PRETR1, which is a nucleic acid having the sequence of SEQ ID NO:7, which is as follows:

5' CAG TTC CTT GCC CAG TGT CCT CTT 3'

Preferably, the primers PRETF1 and PRETR1 are used as a primer pair to amplify a 187 basepair gag sequence of PERV by a nucleic acid amplification method such as the polymerase chain reaction.

Another preferred probe is the pol sequence probe PK15GP1, which is a nucleic acid having the sequence of SEQ ID NO:8, which is as follows:

5' CCA AGA TGG GAG C(A/T)C AAA TTT CTT 3'

An additional preferred probe is the gag sequence probe PRETP2, which is a nucleic acid having the sequence of SEQ ID NO:9, which is as follows:

5' GGC AAT AGG ACC CCA CTC GAC AAG 3'

In accordance with the method for the detection of PERV in a biological sample, a primer pair specific for PERV RNA or DNA, as described above, is incubated with the biological sample for a sufficient amount of time under conditions for the amplification of PERV RNA or DNA. The amplified PERV RNA or DNA is then detected with a probe, as described above, which has been labeled with a detectable label in accordance with methods well known to those skilled in the art. Detection of the label indicates the presence of PERV RNA or DNA in the sample.

Preferably, nucleic acids in the biological sample are extracted according to procedures known to those skilled in the art, such as the procedure of Mulder et al., *J. Clin. Micro.* 32:292–300 (1994) which is incorporated herein by reference.

The biological sample to be tested or analyzed may be obtained from any biological source and is preferably taken from a human who has received a xenotransplant. In addition, the biological sample may be a biological product derived from a donor pig, such as compositions comprising pig factor VIII, or porcine insulin, or porcine heparin. For example, the sample may be a cell sample, tissue sample or biological fluid, such as whole blood, blood serum, blood plasma, urine, semen, saliva, sputum, cerebrospinal fluid, lacrimal fluid, fermentation fluid, lymph fluid, tissue culture fluid, ascites fluid, synovial fluid, pleural fluid, and the like. The most preferred samples are blood plasma or serum. The biological sample may also be a laboratory research sample such as a cell culture supernatant, viral isolate or viral concentrate. The sample is collected or obtained using methods well known to those skilled in the art.

The preferred amplification method is polymerase chain reaction (PCR). However, it will be understood by those skilled in the art that alternative amplification methods could also be employed. Examples of techniques sufficient to direct persons of skill through such in vitro amplification methods, including PCR, the ligase chain reaction (LCR), Q-beta-replicase amplification, and other RNA polymerase mediated techniques (e.g., NASBA) are found in Sambrook et al. (1989) *Molecular Cloning—A Laboratory Manual* (2nd ed.) Vol. 1–3, Cold Spring Harbor Laboratory, Cold Spring Harbor Press, NY, which is incorporated by reference herein, as well as U.S. Pat. No. 4,683,202 to Mullis et al., and other sources well known to those skilled in the art.

The particular label or detectable group attached to the probe is not a critical aspect of the method. The detectable group can be any material having a detectable physical or chemical property. Thus, a label is any composition detectable by spectroscopic, photochemical, biochemical, immunochemical, electrical, optical or chemical means. Useful labels include magnetic beads; fluorescent dyes, such as fluorescein isothiocyanate, Texas red, rhodamine, and the like; radiolabels such as $^3H$, $^{125}I$, $^{131}I$, $^{35}S$, $^{14}C$, or $^{32}P$; enzymes such as LacZ, CAT, horseradish peroxidase, alkaline phosphatase and others commonly used as detectable enzymes, either in an enzyme immunoassay (EIA) or in an enzyme linked immunosorbent assay (ELISA); and calorimetric labels such as colloidal gold or colored glass or plastic, such as polystyrene, polypropylene, or latex beads. The label may be coupled directly or indirectly to the probe according to methods well known in the art. As indicated above, a wide variety of labels may be used, with the choice of label depending on the sensitivity required, ease of conjugation of the compound, stability requirements, available instrumentation, and disposal provisions.

Detection may proceed by any known method, such as immunoblotting, Western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The preferred method of detection is by standard Southern blot hybridization to one or more probes.

In accordance with the method for the detection of PERV in a biological sample, a primer pair specific for PERV DNA, as described above, is incubated with the biological sample for a sufficient amount of time under conditions for the amplification of PERV DNA. The amplified PERV DNA is then detected with a probe, as described above, which has been labeled with a detectable label in accordance with methods well known to those skilled in the art. Detection of the label indicates the presence of PERV DNA in the sample. A preferred method for such detection is PCR.

To differentiate between true xenogeneic PERV infection and pig cell microchimerism, peripheral blood lymphocytes (PBLs) are diluted to a single cell, cell dilutions are lysed to obtain DNA for PCR amplification, and then the end point titers of the PCR amplification of PERV sequences are compared to the end point titers of PCR amplification pig mtDNA sequences. A higher titer for PERV sequences indicates a xenogeneic infection, while comparable titers for both PERV and pig mtDNA sequences would suggest microchimerism. FIG. 2 shows the results of a representative experiment.

Devices

Devices for the detection of porcine mtDNA include solid phase substances such as beads, dipsticks, membranes, microtiter plates or test tubes that have been coated with one or more of the probes described herein, preferably SEQ ID NOS: 1–3. After incubating a sample believed to contain porcine cellular products, particularly porcine mtDNA, with a primer pair, the reagents are transferred to the probe-coated device. If the nucleic acid to be detected is present in the sample, it will hybridize to the probe. The bound nucleic acid is then detected by conventional methods for the detection of nucleic acid molecules in general employing a reagent that need not be specific for porcine mtDNA.

Devices for the detection of PERV RNA and DNA include solid phase substances such as beads, dipsticks, microtiter plates or test tubes that have been coated with one or more of the probes described herein, preferably SEQ ID NOS:4–9. After incubating a sample believed to contain either PERV RNA or DNA with a primer pair, the reagents are transferred to the probe-coated device. If the nucleic acid to be detected is present in the sample, it will hybridize to the probe. The bound nucleic acid is then detected by conventional methods for the detection of nucleic acid molecules in general employing a reagent that need not be specific for PERV RNA or DNA.

The devices may also include elements for detection of PERV sequences or include separate elements for detection of PERV sequences.

Xenograft Detection and Prognosis

The compositions, methods and devices described herein can be used to detect the presence of a xenotransplant to determine whether the xenotransplant is present and is persisting within the recipient. The compositions, methods and devices can also be used, as described above, to detect the presence of porcine mtDNA in a patient who has received a xenotransplant to monitor the survival or rejection of the xenograft. The term "patient" as used herein includes both human and animal xenotransplant recipients.

Furthermore, by conducting simultaneous or sequential analyses on a biological sample for both the presence of PERV nucleic acids and the presence of porcine mtDNA, the compositions, methods and devices described herein can be used to distinguish or differentiate the presence of animal donor cells, indicating graft survival, from the presence of a true zoonotic infection by viruses that may be present in the animal donor cells.

Closely monitored prospective trials utilizing the present invention allow a more comprehensive evaluation of the possibility of cross-species transmission of PERV, and even allow comparison of the PERV:pig mtDNA ratio for a given patient to that obtained from a specific source pig, thereby increasing the reliability with which infection could be distinguished from microchimerism. The present invention can be used in closely monitored clinical trials to assess the safety and efficacy of using porcine cells, tissues, or organs therapeutically in humans.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Cell Lines, Pig Sera, Sample Preparation and Plasmid Cloning

Cells and tissue culture supernatants used in the PCR and RT-PCR analyses, in this example and the examples set forth below, unless indicated otherwise, were generated from the porcine kidney epithelial cell line, PK15 (American Type Culture Collection, ATCC CCL-33), the malignant swine lymphoma-derived cell line, Shimozuma-1 (from Dr. Iwao Suzuka, Tsukaba City, Japan), and PERV-infected 293 human embryonic kidney cells and uninfected 293 cells (from Dr. Robin Weiss, London, UK). Human, baboon, and macaque PBL were obtained by ficoll-hypaque centrifugation of EDTA preserved whole blood. All cell lines were maintained in minimal essential medium using standard tissue culture technique. Tissue culture supernatants containing PERV were harvested every 3 to 4 days and stored at −80° C. Pig serum samples were provided by Drs. Michael Lairmore and Collin Weber.

All cell lines and PBLs were lysed at a concentration of $6 \times 10^6$ cells/mL by proteinase K digestion and stored frozen at −20° C. PERV gag and pol, and pig mtDNA sequences were cloned into plasmids to generate known copy numbers of each target sequence for use in sensitivity analysis of each PCR assay. Target sequences were first PCR amplified from pig PK15 DNA as described below. The amplicons were then cloned into Novagen's pT7blue vector according to the instructions of the manufacturer and plasmid DNA from recombinants was prepared using the Qiagen midiprep kit.

EXAMPLE 2

PCR Analysis of PERV Sequences

In order to detect PERV sequences in clinical samples from pig xenograft recipients, PCR assays targeting two sequences were developed, one in the polymerase (pol) gene and one in the gag gene. PERV sequences in the gag and pol genes (GenBank accession number AF000572), determined from a PERV molecular clone derived from Shimozuma-1 pig cells (Tsukuba-1) in the inventors' lab, were aligned with PERV sequences recently reported from PK15 and MPK cell lines, genomic pig DNA, and additional PERV sequences described recently (GenBank accession numbers U77599, U77600, X99933) to identify conserved regions for design of PCR primers and probes. Wobble bases (N/N) and inosines (I) were used to accommodate nucleotide variability at certain positions in these oligos.

The primers PK15GF2, 5' CCA CAG GGC AAC (G/A) (G/A)C AGT ATC CAT G 3' (SEQ ID NO:4), and PK15GR2, 5' TTG GAG GGT CAA CAC AGT GAT IGG 3' (SEQ ID NO:5), were used to amplify a 212-bp pol sequence and the primers PRETF1, 5' CGG CAA GAG AAG AAT TTG ACT AAG ATC 3' (SEQ ID NO:6), and PRETR1, 5' CAG TTC CTT GCC CAG TGT CCT CTT 3' (SEQ ID NO:7), were used to amplify a 187-bp gag sequence.

To evaluate the sensitivity of both PCR assays, plasmid clones containing 10,000 to 0.1 copies of each target sequence were diluted in a background of human PBL DNA lysates and then PCR amplified. In addition, endpoint dilutions of PK15 DNA lysates from 150,000 to 0.015 cells were prepared in lysates from human PBL and were subjected to amplification. Negative amplification controls for each assay included water and a normal human PBL lysate. PCR was performed with standard conditions of 1 minute at 94° C., 1 minute at 55° C., and 1 minute at 72° C. for 35 cycles using 25 µl of DNA template in 100 µl reaction volumes containing PCR reaction buffer (PRB) (10 mM Tris-HCl, pH 8.3, 50 mM KCL, 1.5 mM MgCl$_2$), 2.5 units Taq polymerase, 1.25 mM of each dNTP, and 100 ng of each oligoprimer. Twenty µl of the PCR products were electrophoresed on a 1.8% agarose gel that was Southern blot hybridization with the $^{32}$P-end-labeled internal oligoprobes PK15GP1, 5' CCA AGA TGG GAG C(A/T)C AAA TTT CTT 3' (SEQ ID NO:8) and PRETP2, 5' GGC AAT AGG ACC CCA CTC GAC AAG 3' (SEQ ID NO:9), respectively. All PCR assays were performed following recommended precautions to prevent contamination.

EXAMPLE 3

PCR Analysis of Proviral PERV DNA Sequences

Figure 4:
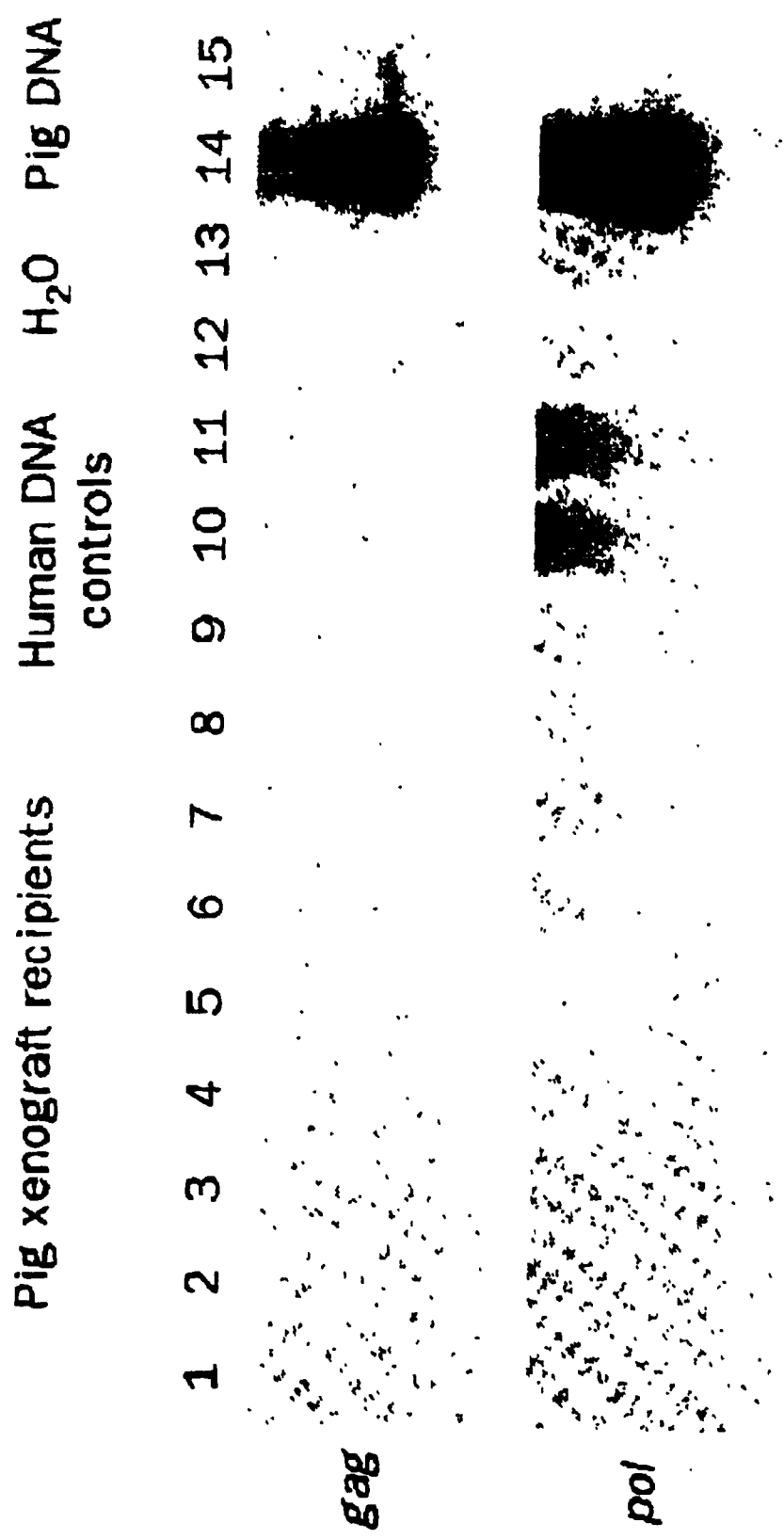
FIG. 4 is a PCR analysis of peripheral blood lymphocytes from pig xenograft recipients for porcine endogenous retroviral gag and pol sequences. Lanes 1 to 8 are results for samples collected in 8/97 from persons XIT1 and XIT3 to XIT9 (samples from persons XIT2 and XIT10 were unavailable), lanes 9 to 11, PERV-uninfected cellular DNA controls; lanes 12 and 13, negative PCR reaction controls with water; lanes 14 and 15 are positive DNA controls from porcine PK15 cell lysates representing DNA equivalents of 1.5 and 0.015 cell, respectively.

Cryopreserved peripheral blood lymphocytes (PBLs) were lysed with proteinase K digestion and the quality of the lysates to support PCR amplification was first confirmed by PCR amplification with beta globin primers as taught by Heneine et al., *J. Clin. Microbiol.* 1992, 30:1605–7. PBL lysates were then tested for the presence of two PERV proviral sequences from the gag and polymerase (pol) viral regions, respectively by using two PCR assays with validated sensitivity and specificity. The primers and probes for both assays were based on conserved PERV sequences identified from an alignment of all known PERV variant sequences determined in our laboratory (from a PERV molecular clone derived from Shimozuma-1 pig cells, provided by I. Suzuka, Tsukuba city, Japan as described in Suzuka et al., FEBS 1986; 198:339–343), or recently reported from PK15, MPK, and other cells as taught by Patience et al., *Nature Med.* 1997, 3:282–6, Wilson et al., *J. Virol.* 1998, 72:3082–7, and Akiyoshi, et al., *J. Virol.* 1998, 72:4503–7. Wobble bases and inosines (I) were used to accommodate nucleotide variability at certain positions in these oligos. A 212-bp sequence was amplified by the following pol primers: PK15GF2 5' CCA CAG GGC AAC (G/A)(G/A)C AGT ATC CAT G 3' (SEQ ID NO:4), and PK15GR2, 5' TTG GAG GGT CAA CAC AGT GAT IGG 3' (SEQ ID NO:5). A 187-bp gag sequence was amplified by PRETF1 5' CGG CAA GAG AAG AAT TTG ACT AAG ATC 3' (SEQ ID NO:6), and PRETR1, 5' CAG TTC CTT GCC CAG TGT CCT CTT 3' (SEQ ID NO:7). Aliquots of lysates containing DNA from 150,000 PBLs were subjected to 35 cycles of amplification under standard methods as taught by Heneine et al., *J. Clin. Microbiol.* 1992, 30:1605–7. Detection of PCR products was done by standard Southern blot hybridization to $^{32}$P-endlabeled internal, oligoprobes PK15GP1 5' CCA AGA TGG GAG C(A/T)C AAA TTT CTT 3' (SEQ ID NO:8) and PRETP2 sequence is 5' GGC AAT AGG ACC CCA CTC GAC AAG 3' (SEQ ID NO:9) for the pol and gag sequences, respectively. Negative control reactions included water and uninfected human PBL lysate. Positive control reactions consisted of uninfected human PBL lysate spiked with DNA lysate from 1.5 and 0.015 pig PK15 cells (prepared by diluting lysates of PK15 cells in buffer). The PCR reaction with the DNA equivalent of 0.15 PK15 cell represents the detection limit of the assays and is used as a sensitivity control in each experiment. Experiments were considered acceptable when appropriate results were seen in all negative and positive controls. The results are shown in FIG. 4.

EXAMPLE 4

Amplification of Pig-specific Mitochondrial Sequences

Since PERV sequences are present in all pig cells microchimerism can result in positive PERV PCR results which will complicate diagnostic interpretation of these results in samples from xenograft recipients. Thus, in order to distinguish between the presence of donor pig cells containing PERV sequences and true xenogeneic PERV infection, a PCR assay was developed to detect pig-specific mtDNA sequences in clinical samples from xenograft recipients. The cytochrome oxidase subunit II (COII) mtDNA sequence (GenBank accession number U18827) was chosen as a target sequence because this gene has a high degree of variability (70.5%) from the human mtDNA sequence. The porcine mtDNA COII sequence was aligned with that of human, as well as that of macaque (*Macaca mulatta*), and baboon (*Papio* species); two nonhuman primate species (GenBank accession numbers M25171, J02825, and M74007, respectively). Regions of sequence divergence were identified and used for the design of the primers PMTF2, 5' TCA CCC ATC ATA GAA GAA CTC CTA CA 3' (SEQ ID NO:1), and PMTR2, 5' TTT TAC GGT TAA GGC TGG GTT ATT AAT T 3' (SEQ ID NO:2) that generate a 255-bp pig-specific mtDNA COII sequence. The pig-specific internal oligoprobe PMTP1, 5' GAC ACA CAC TAG CAC AAT GGA TGC 3' (SEQ ID NO:3) was used for detection of the amplified product. Like both PERV PCR assays the sensitivity of the pig mtDNA primers was evaluated on known numbers of plasmid copies of pig mtDNA sequences as well as on dilutions of pig PK15 cell lysates, both of which were diluted in a background of human PBL DNA lysates.

Results of PCR amplification of the PERV specific and pig mtDNA sequences are shown in FIG. 1. All three assays were highly sensitive. The gag and pol primers were sensitive to one and five copies of PERV gag and pol sequences, respectively. The porcine mtDNA PCR assay was also capable of detecting a single copy of pig mtDNA sequences. This level of sensitivity of the pig-specific PCR mtDNA PCR assay is at least one log more sensitive than other pig-specific PCR assays that use low-copy DNA target sequences. When pig DNA lysates were tested, the PERV pol and gag primers were able to detect the equivalent of DNA from 0.15 PK15 cells in a background of DNA from 150,000 human PBLs and the pig mtDNA primers could detect the equivalent of DNA from 0.015 PK15 cells in an equivalent amount of background DNA. This level of detection for all three PCR assays was repeatedly obtained and the end point dilution of 0.15 or 0.015 PK15 DNA equivalents was included as a sensitivity control in all PERV and pig mtDNA PCR assays, respectively.

EXAMPLE 5

Evaluation of the Specificity of the PERV and Pig mtDNA PCR Assays on PBL from Human and Nonhuman Primates The specificity of both the PERV and pig mtDNA PCR assays was determined by testing DNA lysates from PBLs collected from 69 randomly selected anonymous U.S. blood donors and 6 macaques (*Macaca mulatta*) and 6 baboons (3 *Papio anubis* and 3 *Papio hamadryas*).

The PERV gag and pol and the pig mtDNA PCR assay results were all negative for the 69 human PBL samples from U.S. blood donors and for the PBL samples from the 6 baboons and 6 rhesus macaques. Representative results are shown in FIG. 1. These negative results demonstrate the high specificity of the PERV and pig mtDNA PCR assay and their suitability for the study of PERV transmission and chimerism in these three primate species.

EXAMPLE 6

Determination of the Reproducibility and Predictive Value of the PERV and Pig mtDNA PCR Assays The false negative rate for each PCR assay was determined by repeat testing of pig DNA from PK15 cell lysates at the limit of detection in a background of DNA from human PBL lysates. The false negative rate for each PCR assay was determined by dividing the number of replicates testing negative by the total number of replicates.

Analysis of 70 replicate tests at the detection threshold of the PERV gag and pol, and the pig mtDNA PCR assays showed a false negative rate of 1.4%, 4.3%, and 0%, respectively. These results were obtained despite performing the assays with conditions that simulate the day to day changing test parameters inherent in routine laboratory PCR testing. These results show that the PERV and pig mtDNA PCR assays were very reproducible.

The sensitivity and specificity of these assays were determined by testing DNA lysates from PBLs collected from 81 unexposed primates (69 human blood donors, 6 macaques, and 6 baboons) and 70 replicate positive samples (DNA from human PBL lysates containing input pig DNA from PK15 cell lysates at the level of detection of the assay) as previously described. This testing defined the sensitivity (true-positive results/true-positive and false-negative results) of the gag, pol, and pig COII assays at 98.6%, 95.7%, and 100%, respectively. The same testing defined specificity (true-negative results/false-positive and true-negative results) of all three assays at 100%.

PERV and pig mtDNA was present at the previously defined limits of detection of these assays in 70 of these 151 tested specimens. The predictive value of negative test results when these assays were applied to specimens that contained PERV and pig DNA at a 46% prevalence rate was 98.8%, 96.4%, and 100% for the gag, pol, and pig COII assays, respectively. The predictive value of a positive test results applied to this same specimen collection was 100% for all three assays.

EXAMPLE 7

PCR Detection of Pig Cell-specific Sequences

To monitor for the presence of pig cell-specific sequences, a PCR assay was developed to detect pig DNA sequences in serum samples. The nucleic acids were extracted according to the procedure of Mulder et al., *J. Clin. Micro.* 1994, 32:292. Briefly, 200 µl human or pig cell donor recipient (such as non-human primate) sera were mixed with three volumes of lysis solution (5.75 M GuSCN, 50 mM Tris HCl pH 7.5, 100 mM β-mercaptoethanol) and incubated at room temperature for 10 minutes. Nucleic acids were precipitated and resuspended in 50 µof diethlypyrocarbonate-treated water. PCR amplification was performed as described above using 10 µl extracted nucleic acids, the PMTF2 and PMTR2 primers, the PCR amplification conditions as described above, and the PMTP1 probe.

A 255-bp sequence from the porcine cytochrome oxidase subunit II (COII) gene was selected for analysis, and was amplified in DNA extracts of 25 µl of serum by the oligoprimers PMTF2, 5' TCA CCC ATC ATA GAA GAA CTC CTA CA 3' (SEQ ID NO:1), and PMTR2, 5' TTT TAC GGT TAA GGC TGG GTT ATT AAT T 3' (SEQ ID NO:2) using standard PCR conditions. The PCR product was detected by Southern blot hybridization to the a 32-P-labeled internal oligoprobe PMTP1, 5' GAC ACA CAC TAG CAC AAT GGA TGC 3' (SEQ ID NO:3). Sera from unexposed humans were used as negative controls. Sera from pigs, DNA lysates of pig PK15 cells or PK15 culture fluids were used as positive controls for mtDNA analysis.

EXAMPLE 8

A Test Algorithm for Differentiating Between Xenogeneic PERV Infection and Microchimerism As depicted in FIG. 2, panel C, the PERV and pig mtDNA assays were integrated in a test algorithm to distinguish between true xenogeneic PERV infection and pig cell microchimerism. This algorithm was based on comparing, in the clinical PBL samples, the level of pig source cells with that of PERV-infected recipient cells. Levels of both cells are determined by endpoint dilution of the PBLs in the test sample and subsequent PCR analysis of the PBL dilutions for both PERV and pig mtDNA sequences. A higher titer for PERV sequences suggests xenogeneic infection, while comparable titers for both PERV and pig mtDNA sequences suggest pig cell microchimerism. FIG. 2 shows the results of a representative experiment designed to test this method in two diagnostic possibilities. The first possibility represents the presence of xenogeneic infection with minimal microchimerism and the second possibility illustrates microchimerism without PERV infection. To test the first diagnostic possibility, cell suspensions containing 100,000 PERV-infected human 293 cells and one pig PBL were prepared and then endpoint diluted to a single cell level. All cell dilutions were then lysed, and the DNA was tested for PERV gag and pig mtDNA sequences. To test the second diagnostic possibility, cell suspensions containing 100,000 pig PBLs alone were similarly prepared and tested. As expected, the first set of samples showed a much higher level of PERV gag sequences (FIG. 2, panel A) than pig mtDNA sequences (FIG. 2, panel B), demonstrating the presence of PERV-infected cells. In contrast, the second sample set showed equivalent titers of PERV gag and pig mtDNA sequences, suggesting the presence of pig cells in the absence of PERV infection. These results show the usefulness of this method in distinguishing xenogeneic infection from pig cell microchimerism.

EXAMPLE 9

Detection of PERV RNA in Patient Sera

Serum nucleic acids were extracted according to the procedure of Mulder et al., *J. Clin. Micro.* 1994, 32:292. An aliquot of the extract was used for PCR analysis of porcine mtDNA (see below), and the rest was digested with ten units of RNase-free DNase-I (Boehringer-Mannheim) for one hour at 37° C. in DNase buffer (5 mM Tris-HCl pH 8.3, 1.0 mM $MgCl_2$, 0.01 mM DTT, 1 U/µl RNasin), and followed by inactivation of the DNase by boiling for five minutes. RNA extracts corresponding to 200 µl serum (for samples collected between 4–7 years post-transplant) or 50 µl serum (for samples collected during the first year after the transplant) were tested for PERV gag RNA by RT-PCR. Control PCR reactions which received no RT were included for each sample to confirm that a positive result was due to the presence of PERV RNA, and not the result of residual contamination with PERV genomic DNA. Reverse transcription was primed with PRETR1 in the presence 50 U murine leukemia virus RT and standard conditions. Following incubation at 37° C. for two hours, RT was inactivated by heating and the reaction was PCR-amplified in the presence of PRETF1 as described above. The PERV gag amplicon was detected by probing with PRETP2. Positive controls for the RT-PCR assay included DNA-free RNA extracts from tissue culture supernatants from the PK15 or Shimozuma-1 cell lines. Controls for the performance of DNase digestion included PCR reactions containing DNase-treated and DNase-untreated genomic DNA from pig PK15cells. Experiments were considered acceptable when appropriate results from all controls were obtained. PERV RNA can also be detected with the PK15GF2 and PK15GR2 primers and the PK15GP1 probe by using similar conditions as described above.

Figure 3:
FIG. 3 is a PCR analysis of pig serum and tissue culture supernatants from pig cell lines for PERV RNA gag sequences. RT-PCR results in the presence (+RT) or absence (−RT) of RT: lanes 1–4 are human sera negative for human immunodeficiency virus types 1 and 2 and human T cell lymphotropic virus types 1 and 2; lanes 5 to 7 are pig serum samples; lanes 8 to 13 are PERV RNA from PK15 tissue culture supernatant 10-fold serially diluted from $10^{-1}$ to $10^{-6}$, respectively; lane 14, uninfected culture medium control.

FIG. 3 shows representative RT-PCR test results of PERV gag RNA in PERV-positive culture supernatants and in pig serum samples. The assay detected RNA at a $10^{-5}$ dilution of culture supernatant or the equivalent of 0.002 µl. The undiluted culture fluid had $5.5 \times 10^{-4}$ U/ml of RT activity, determined from a standard curve by using HIV-1 RT as previously described. The RT-PCR assay also detected the presence of PERV RNA in 18 of 20 (90%) pig serum samples.

EXAMPLE 10

Screening for RT Activity in Serum

RT detection was done by using the Amp-RT assay, an ultrasensitive PCR-based RT assay as taught by Heneine et al., *J. Inf Dis.* 1995, 171:1210–6; Garcia Lerma et al., *J. Inf. Dis.* 1998, 177:1221–9; and Yamamoto et al., *J. Viro Methods* 1996, 61, 135–143. Amp-RT analysis of sera from patients or pigs was done in duplicate tests on ultracentrifuged pellets equivalent to 10 µl serum as previously described in the above-cited references. Amp-RT products were detected by Southern blot hybridization. Results were considered positive when both duplicate tests were positive.

Figure 6:
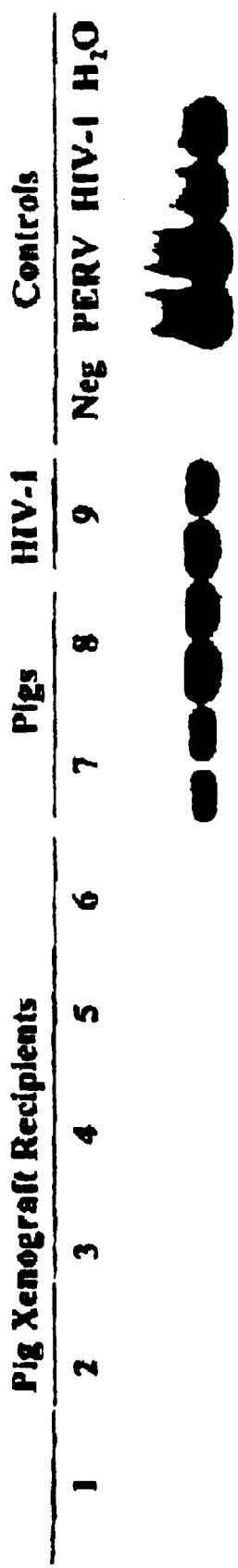
FIG. 6 is an analysis of reverse transcriptase (RT) activity by the Amp-RT assay in serum from pig xenograft recipients, pig sera, and an HIV-1-infected person. Lanes 1 to 6 are results of duplicate testing from six pig xenograft patients (XIT1 and XIT3 to XIT7, respectively); lanes 7 and 8, are results from two pig sera; lane 9, results from one HIV-1-infected person. Controls are: serum from HIV-1/2 and HTLV-I/II antibody negative individual (Neg); PERV, PK15 culture supernatant containing porcine endogenous retrovirus; HIV-I, human immunodeficiency virus in culture medium; H₂O, water as negative control.

For each Amp-RT experiment positive controls included culture supernatants containing PERV (obtained from PK-15 cells) and the human immunodeficiency virus type 1 (HIV-1) (FIG. 6). Negative controls included water and a human serum sample that is antibody negative to all known human retroviruses (HIV-1, HIV-2, and the human T-cell lymphotropic virus types 1 and 2, HTLV-I and HTLV-II) (FIG. 6). Two sets of human sera unrelated to the xenograft recipients were also tested. The first set included 35 serum samples of HIV-1 seropositive persons who were all asymptomatic and had normal counts of CD4-positive cells (>500/µl). The second group of samples included 15 serum specimens from U.S. blood donors who are seronegative for HIV-1, HIV-2, HTLV-I, and HTLV-II. Twelve serum samples from pigs were also tested for the presence of RT activity. Representative results depicted in FIG. 6 show the lack of RT activity in xenograft recipients.

EXAMPLE 11

Serologic Screening for Antibodies to PERV

Whole cell lysates derived from human kidney 293 cells infected with PERV-PK15 (provided by Robin A. Weiss and described by Patience et al., *Nature Med.* 1997, 3:282–6) were used as a source of PERV antigen. Blots were reacted for three hours at either 1:50 dilution of patient sera, or a 1:100 dilution of control antisera followed by a 1:7,000 dilution of protein A/G horse radish peroxidase (Pierce, Buckinghamshire, England) for 1.5 hours. Blots were visualized by chemiluminescence using ECL Western blotting reagents (Amersham, Rockford, Ill.). Based on the reported cross-reactivity between the gag antigens of PERV and simian sarcoma associated virus (SSAV, a retrovirus that is highly related to the gibbon ape leukemia virus), a goat anti-SSAV p29 antiserum was used as a positive control antiserum. This antiserum shows strong reactivity to the PERV p30 found in 293 PERV-PK cells, and no reactivity to uninfected 293 cells.

EXAMPLE 12

Xenograftin and Clinical Follow-up of Patients

Ten patients (mean age 40 years) with long-standing insulin dependent diabetes (mean duration 30 years) and end-stage diabetic nephropathy underwent transplantation with fetal porcine pancreatic islet-like cell clusters (ICC) between June 1990 and April 1993 as described by Groth et al., Lancet 1994, 344:1402–4. Patients were given between 200,000–1,000.000 ICC, which represent around $4 \times 10^8$ to $2 \times 10^9$ cells based on an estimate of 2,000 cells per ICC. The first eight patients had undergone renal transplantation two to seven years earlier; all eight were given the ICCs by intraportal injection. Two other patients received the ICCs under the capsule of a simultaneously transplanted kidney graft. Cyclosporine, prednisolone, and azathioprine was used for maintenance immunosuppression in nine patients, while one patient received prednisolone and azathioprine only. At the time of the xenoislet transplantation, five patients were given adjunctive immunosuppressive treatment with rabbit-antithymocyte globulin while five other patients were given 15-deoxyspergualin.

Evidence of survival of the porcine cells in patients previously found included detection of low levels of porcine C-peptide in urine in four patients lasting until 250 to 450 days after islet transplantation (see Table 2 below in Example 14). A renal biopsy obtained three weeks after transplantation from a fifth patient (XIT10) who received ICC under the renal capsule revealed clusters of epithelial cells which stained positively for insulin, glucagon and chromogranin, demonstrating cell viability and ability to produce insulin as taught by Tibell et al., *Transplant Proc.* 1994, 26:1121.

All patients have been followed up regularly during the 4.5–7.5 years after xenoislet transplantation. During the first year, no patient was hospitalized for febrile disease. Subsequently, one patient who was suffering from chronic asthma was hospitalized several times for pneumonia. Six patients have been treated for infectious diabetic ulcers with concomitant local infections. Also, there has been several instances of lower urinary tract infections, and one patient was treated for Klebsiella septicemia four years after transplantation. Two patients (XIT2 and XIT10) died of myocardial infarction 2.5 and 5 years after the xenotransplantation. One patient (XIT4) lost a renal graft in chronic rejection. This event occurred 12 years after the renal transplantation, and six years after the xenoislet transplantation. The mortality and morbidity was not different than that seen in diabetic renal transplant recipients. None of the patients had signs of lymphoproliferative disease or neurological disease of the kind associated with C-type retroviruses in humans or animals.

EXAMPLE 13

PCR Analysis of PERV Sequences in Xenolgraft Recipients

Table 1 below summarizes the results of PCR testing for PERV proviral sequences in PBLs. Samples collected from patient XIT2 and XIT10 at one time point, and from the remaining eight patients at two or three time points, were all negative for both gag and pol PERV sequences. All PBL samples had competent DNA that is optimally amplifiable with beta globin primers (data not shown). Representative PCR results are shown in FIG. 4. Lane 15 shows the signal from the sensitivity control included in each experiment. These results do not support the presence of PERV infection in PBLs.

TABLE 1

PCR analysis of porcine endogenous retrovirus (PERV) proviral sequences in peripheral blood lymphocyte samples from 10 diabetic patients (MT 1 to MT 10) who received pig islet cell xenografts between June 1990 and April 1993.

| Months Post Transplantation | Time of Sampling | PERV Sequences[a] gag | pol |
|---|---|---|---|
| 32 to 60 | April 1995 | 0/9 | 0/9[b] |
| 49 to 83 | April 1997 | 0/8 | 0/8[c] |

[a]Number of positive samples/total tested.
[b]Samples from nine patients (sample from XIT6 not available).
[c]Samples obtained from eight patients (XIT2 and XFP10 not available).

EXAMPLE 14

Detection of PERV RNA and Porcine Mitochondrial DNA in Sera of Xenograft Recipients In order to detect the presence of productive infection with PERV, serum of all patients was analyzed for the presence of PERV RNA gag sequences by RT-PCR. Table 2 below summarizes the results of screening of PERV RNA. All patient serum samples collected between three days and seven years after the xenotransplant were negative for PERV RNA demonstrating that PERV expression was absent at both early and late time points after the transplant.

Figures 5A, 5B, 5C:
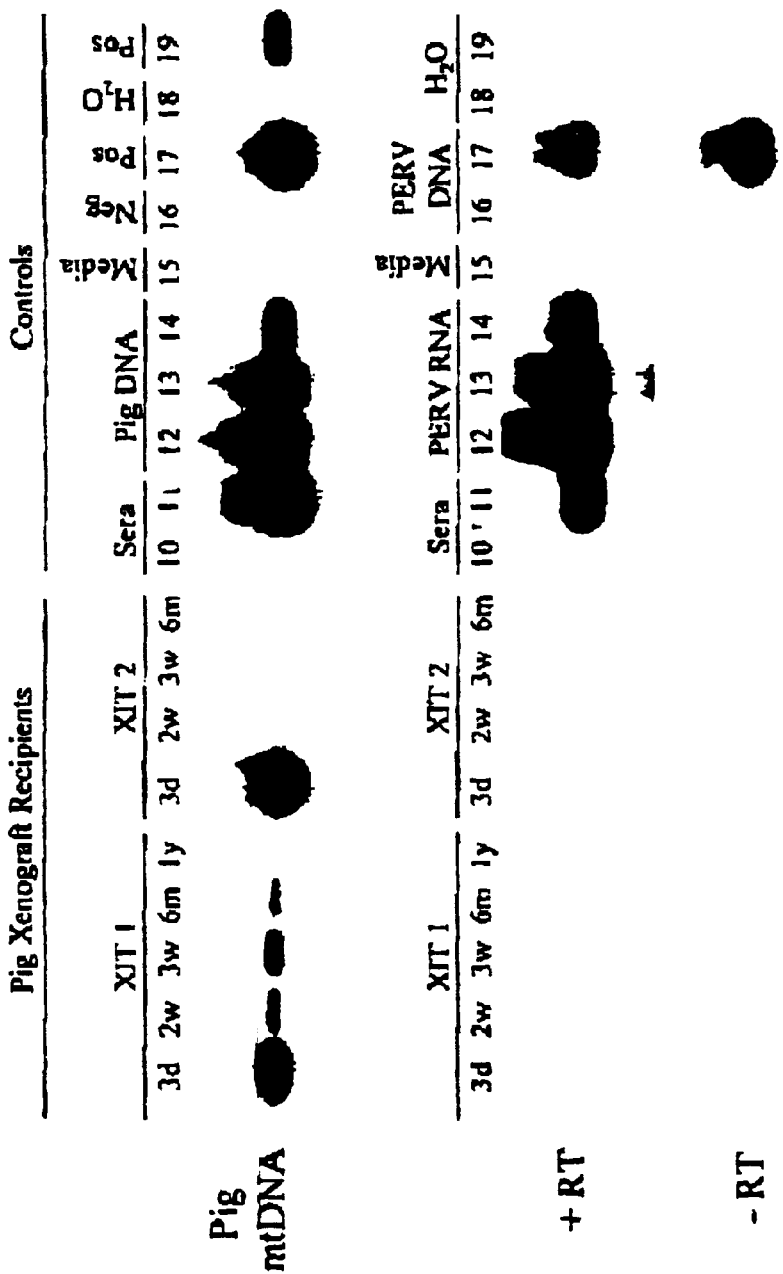
FIG. 5 is a PCR analysis of pig xenograft recipient sera for porcine endogenous retrovirus (PERV) RNA and pig mitochondrial DNA (mtDNA) sequences. Panel A. Pig mtDNA PCR results: lanes 1 to 5, patient XIT1 at days 3,14, 26, 194, 478 post xenograft; lanes 6 to 9, patient XIT2 at days 3, 17, 24 and 178 post xenograft, respectively; lane 10, human serum antibody negative for HIV-1/2 and HTLV-I/II; lane 11, pig serum; lanes 12 to 14, mtDNA from PK15 tissue culture supernatant diluted 10, 100, and 1,000 fold in medium, respectively; lane 15, uninfected culture medium control; lane 16, human cellular DNA negative control; lane 17, pig DNA positive control from PK15 cells; lane 18, water as negative reaction control, lane 19, PCR sensitivity control, pig DNA corresponding to 0.015 PK15 cell lysate. Panel B. RT-PCR results of PERV gag RNA sequences in the presence of reverse transcriptase (+RT): lane assignments are the same as for "A" except lanes 12 to 14 are PERV RNA from PK15 tissue culture supernatant diluted 10, 100, and 1,000 fold in medium, respectively; lanes 16 and 17; DNase treatment control, DNA from 0.15 PK15 cell treated with DNase (lane 16) and DNase untreated (lane 17); lanes 18 and 19 water as negative reaction controls. Panel C. RT-PCR results of PERV gag RNA sequences in the absence of reverse transcriptase (−RT): lane assignments are the same as for "B".

Serum samples were also tested for porcine mtDNA sequences as evidence of pig-specific cellular markers. The high copy number of mitochondria in cells makes detection of mtDNA a more sensitive cellular marker than single-copy genomic sequences. Seven of ten patients receiving pig xenografts had detectable pig cell markers from two days to one year following the xenografting. These results highlight the utility of the pig mtDNA PCR assay in sera to monitor for pig xenograft persistence. Table 2 shows also the test results for porcine mtDNA in the patients' sera. In contrast to PERV RNA, pig mtDNA was detectable in various patients from day three (six patients), up to one year (patient XIT7). Among patients tested 4–7 years after the xenotransplant, none had detectable pig mtDNA. Representative results are shown in FIG. 5 and Table 3. As expected, PCR signals of pig mtDNA from all patients at all time points were consistently weaker than those from pig sera (FIG. 5, Panel A, lane 11). However, the pig mtDNA PCR signals in the patients were strongest at day three (FIG. 5, Panel A), consistent with higher levels of circulating pig source cells in patients' sera during this early period after the xenotransplant compared to later time points. The prevalence of detectable pig mtDNA in sera was also highest at three days (6/10) and decreased gradually over time, also likely reflecting diminishing levels of porcine cells in the patients' circulation. However, the presence of pig mtDNA in serum of 4/10 patients six months after transplant argues for successful persistence of pig cells in these patients, despite the inability to consistently detect mtDNA in 3/4 of these patients at intermediate time points. The detection of urinary excretion of porcine C peptide for more than six months after the transplant in three of these four patients further supports the porcine mtDNA findings. In contrast, excretion of urinary porcine C-peptide was not detectable in any of the five patients who were persistently porcine mtDNA- negative after day three. The inability to detect porcine mtDNA at intermediate time points in three patients likely reflects the presence of low fluctuating levels of porcine mitochondria in the small volumes (25 $\mu$l) of sera tested. The transplant technique may also influence the presence of pig mtDNA in the recipient's circulation: porcine mtDNA was detectable at three days in 6/8 (75%) patients who received intraportal transplants but in neither of two patients who received pig cells implanted under the renal capsule.

TABLE 2

Analysis of serum for the presence of porcine endogenous retrovirus (PERV) RNA, reverse transcriptase (RT) activity, and pig mitochondrial sequences (pig mtDNA) from 10 diabetic patients (XIT1 to XIT10) who received pig islet cell xenografts. Positive and negative control sera were obtained from HIV-infected persons, and HIV-1,-2 and HTLV-I,-II (HIV/HTLV) seronegative U.S. blood donors, respectively.

| Porcine islet Recipients Time Post Transplantation | RT # positive patients/total | PERV RNA # positive patients/total | Pig mtDNA # positive patients/total |
|---|---|---|---|
| 2 days to 6 mo | 0/8[a] | 0/10 | 7/10 |
| 49 to 83 mo | 0/8[b] | 0/8[2] | 0/8[2] |
| 52 to 86 mo | 0/8[b] | 0/8[2] | ND |
| HIV-1 seropositive | 26/35(74.2%) | ND | ND |
| HIV/HTLV seronegative | 0/15 | ND | ND |

[a]The eight samples were from two patients (XIT7 and XIT8) at 2 days, 13 days, 27 days, and approximately 6 months after transplantation, respectively.
[b]Samples obtained from eight surviving patients (XIT1, XIT3 to XIT9).

TABLE 3

PCR analysis of pig mtDNA sequences in sera from 10 diabetic patients given pig islet cells.

| | pig mtDNA[a] | | | | | |
|---|---|---|---|---|---|---|
| Patient | 2–3 days | 2 weeks | 3 weeks | 6 months | 1 year | 4–7[b] years |
| XIT1 | + | + | + | + | − | − |
| XIT2 | + | − | − | − | NA | NA |
| XIT3 | − | NA | − | − | NA | − |
| XIT4 | + | − | − | − | NA | − |
| XIT5 | + | − | − | − | NA | − |
| XIT6 | − | − | − | − | NA | − |
| XIT7 | + | − | − | + | + | − |
| XIT8 | + | + | − | + | − | − |
| XIT9 | − | − | − | − | NA | − |
| XIT10 | − | + | − | + | NA | NA |

| | Transplant characteristics | | |
|---|---|---|---|
| Patient | Evidence of xenoislet survival | Site | ICCs(1000s) |
| XIT1 | C-peptide + | IP | 390 |
| XIT2 | | IP | 520 |
| XIT3 | | IP | 460 |
| XIT4 | | IP | 410 |
| XIT5 | | IP | 330 |
| XIT6 | C-peptide + | IP | 520 |
| XIT7 | C-peptide + | IP | 800 |
| XIT8 | C-peptide + | IP | 1020 |
| XIT9 | | RC | 200 |
| XIT10 | Biopsy + | RC | 410 |

[a]PCR results at time after, xenotransplantation; NA = samples not available.
[b]4–7 year results are for samples collected in both April and August, 1997.
[c]IP = intraportal; RC = renal capsule;. ICC = islet-like cell clusters; C-peptide + = urinary excretion of porcine C-peptide detected; biopsy + = detection of pig cells under renal capsule in biopsy three weeks post-transplant.

EXAMPLE 15

Screening for Reverse Transcriptase Activity in Pig Xenograft Patient's Serum In order to determine expression of retroviruses, serum from all patients was screened for the presence of RT activity, which is a particle-associated enzyme present in all retroviruses. The presence of RT activity in serum is evidence of retroviral expression. Thus, screening for RT activity in serum can detect the presence of PERV as well as unknown porcine retroviruses.

RT activity was not detected in 16 samples obtained from eight patients (XIT1, XIT3 to XIT9) between four and seven years after the transplant. Representative results are shown in FIG. 6. Eight samples obtained from patients XIT7, and XIT8 at 3, 13, 24 days, and about 6 months post transplant, respectively, were also RT-negative as shown in Table 2. Amp-RT testing of 15 HTLV/HIV seronegative controls failed to detect RT activity. In contrast, RT activity was detected in 75% of the sera from the HIV-1 infected controls (FIG. 6, right panel)

EXAMPLE 16

Serologic Screening for Antibodies to PERV in Xenograft Patients

Figure 7:
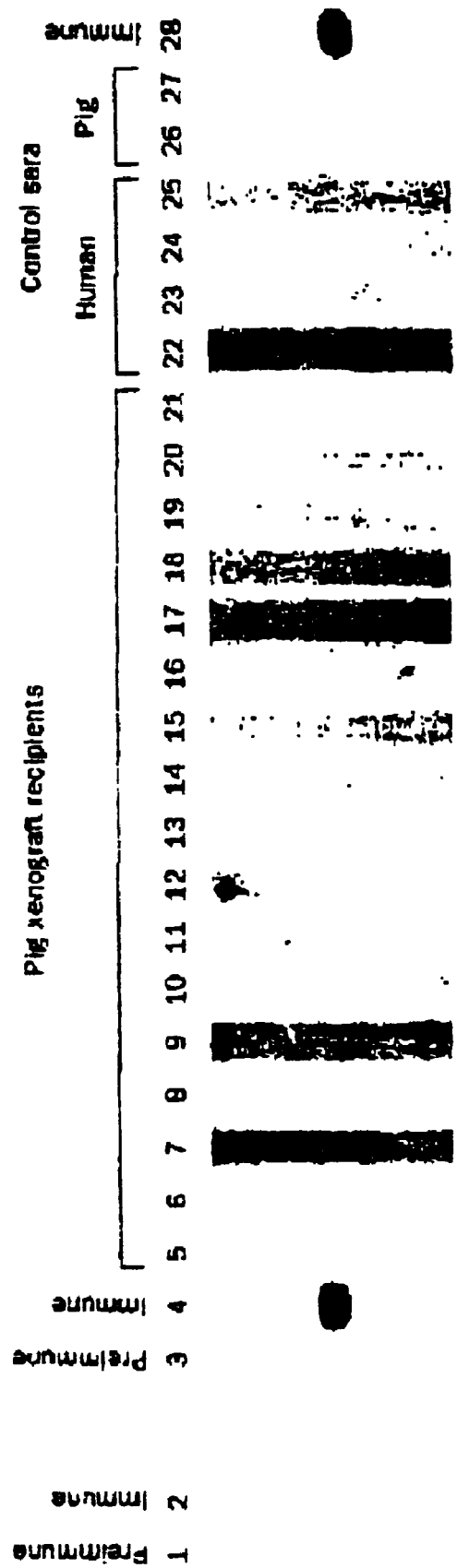
FIG. 7 is a representative Western immunoblot analysis of antibodies to PERV in porcine xenograft recipients, non transplant human controls and pigs. Lanes 1 and 2 are blots from uninfected 293 human kidney cells reacted with pre-immune serum and goat anti-p29 protein of simian sarcoma associated virus (SSAV) serum, respectively. All other lanes represent blots from PERV-infected 293 human kidney cels reacted with: lane 3, preimmune control serum; lane 4 and 28, anti-SSAV p29 immune serum; lanes 5 through 21, sera from porcine xenograft recipients taken 4 to 7 years post transplant; lanes 22–25, control sera from unexposed human blood donors; lanes 26 and 27, pig control sera.

Sera were tested for PERV antibodies by a Western immunoblot assay. Antibodies to p130 PERV protein were not detected in any serum sample collected around six months post transplantation from ten patients. Additional serum samples collected from eight patients from two time points between four and seven years after transplantation were also found to be seronegative. Representative results are shown in FIG. 7. These results demonstrate persistent seronegativity to PERV p30 proteins. Sera from two pigs also tested negative confirming immunologic tolerance to PERV proteins, as expected with an endogenous virus.

EXAMPLE 17

Detection of PERV RNA and RT in Pig Sera

To examine PERV expression in pigs sera from twelve pigs were screened for the presence of PERV RNA sequences. In contrast to the results from the patients, PERV RNA-positive results were seen in 18 of 20 (90%) pig samples (FIG. 5, Panel B, lane 11). The positive results were not due to contamination with genomic DNA since control PCR reactions with no RT were all negative as represented in FIG. 5, Panel C, lane 11. To further confirm the presence of retroviruses in these samples, RT activity was tested for. RT was detected in viral pellets of nine of the twelve sera tested. Representative results from pig sera are shown in FIG. 6, lanes 7 and 8. All nine samples had also detectable PERV RNA, while the three RT-negative samples had undetectable PERV RNA sequences. The strong association seen between detection of RT activity and PERV RNA suggests that the observed RT activity is likely to be related to PERV particles. These results suggest that PERV are released in the sera of pigs.

EXAMPLE 18

Monitoring of Cross-species PERV Transmission

Specimens from 160 patients treated with various living pig tissues from 1 day to over 12 years prior to testing were analyzed to address the concerns about possible cross-species transmission of PERV. PCR for PERV DNA, and Western blot analyses for anti-PERV antibodies were performed at multiple testing sites using the methods, compositions and devices described herein. Persistent microchimerism was demonstrated in 23 patients for up to 8.5 years. No PERV infection was detected in any of these patients.

To investigate the potential transmission of PERV to humans, peripheral blood mononuclear cells (PBMC) and serum from 160 patients who had been treated with living pig tissue were retrospectively studied. One hundred and sixty patients (83 males, 77 females; aged 2–77 years) participated in this study. The patients had previously been treated using one of the following procedures: (a) Extracorporeal splenic perfusion (ECSP) (n=100) through spleens from healthy slaughterhouse pigs as "immunotherapy" for various indications; (b) extracorporeal perfusion for liver failure using the HepatAssist™ device (n=28), which contained pig hepatocytes enclosed in a semi-permeable membrane; (c) pig skin grafts (n=15) for burns; (d) porcine pancreatic islet cell transplants for diabetes (n=14) (evidence of porcine C-peptide (released from islets) was detected in the urine of four patients for 257 to 460 days); (e) extracorporeal pig kidney perfusion (n=2); and (f) extracorporeal perfusion through a whole pig liver (n=1) followed by a liver allotransplant and pharmacological immunosuppression.

No evidence of persistent PERV infection could be detected in any of the 160 patients in this study, including 37 who were pharmacologically immunosuppressed and therefore presumed to be at increased risk of infection.

The absence of identifiable adverse events in any of the 23 patients with identified microchimerism despite 43.7 person-years of cumulative exposure to pig cells is reassuring. The long-term persistence of microchimerism in patients tested between 2 and 102 months after ECSP suggest that it is possible that these pig cells are dendritic cells, as observed in allotransplantation, or stem cells originating from the pig spleen, which may express low levels of the xenoantigen galactose $\alpha$ (1–3) galactose, allowing them to escape antibody mediated clearance. These results demonstrate the utility of the compositions, methods and devices described herein for long-term monitoring of potential PERV transmission in xenotransplant recipients.

All of the publications and references mentioned herein are hereby incorporated by reference.

It should be understood, of course, that the foregoing relates only to preferred embodiments of the present invention and that numerous modifications or alterations may be made therein without departing from the spirit and the scope of the invention as set forth in the present specification.

What is claimed is:

1. A method for the detection of presence or survival of a porcine xenograft in a subject, comprising:

detecting a porcine mitochondrial nucleic acid in a sample from the subject by a polymerase mediated technique utilizing a nucleic acid sequence having a sequence as set forth as SEQ ID NO: 1 or SEQ ID NO: 2, wherein presence of the porcine mitochondrial nucleic acid in the sample demonstrates presence or survival of the porcine xenograft.

2. The method of claim 1, wherein the mitochondrial nucleic acid is deoxyribonucleic acid or ribonucleic acid.

3. The method of claim 1, wherein the porcine mitochondrial nucleic acid encodes a porcine cytochrome oxidase subunit II polypeptide.

4. The method of claim 1, wherein the polymerase mediated technique is polymerase chain reaction.

5. The method of claim 1, wherein presence or survival of the xenograft indicates a lack of rejection of the xenograft.

6. The method of claim 1, wherein the xenograft is a liver xenograft, neuronal tissue xenograft, a kidney xenograft, or an islet cell xenograft.

7. The method of claim 1, wherein the sample is a cell, tissue, blood, plasma, urine, semen, saliva, sputum, cerebrospinal fluid, lacrimal fluid, lymph fluid, synovial fluid, pleural fluid, or serum sample.

8. A method for distinguishing between infection with a xenogeneic porcine retrovirus and pig cell microchimerism in a subject, comprising:

isolating a peripheral blood lymphocyte from the subject;

detecting the presence of a porcine endogenous retroviral nucleic acid; and detecting the presence of a porcine mitochondrial nucleic acid by a polymerase mediated technique utilizing a nucleic acid sequence having a sequence as set forth as SEQ ID NO: 1 or SEQ ID NO: 2;

wherein the comparable amounts of porcine endogenous retroviral nucleic acid and porcine mitochondrial nucleic acid indicate pig cell microchimerism and absence of infection with the xenogeneic porcine retrovirus.

9. The method of claim 8, wherein the detecting of porcine endogenous retroviral nucleic acid is by a polymerase mediated technique.

10. The method of claim 9, wherein the polymerase mediated technique utilizes a nucleic acid having a sequence comprising SEQ ID NO:6 or SEQ ID NO: 7.

11. The method of claim 9, wherein the polymerase mediated technique is polymerase chain reaction.

12. The method of claim 4, wherein the detecting of porcine mitochondrial nucleic acid is by a polymerase mediated technique.

13. The method of claim 8, wherein the porcine mitochondrial nucleic acid encodes a porcine cytochrome oxidase subunit II polypeptide.

14. A method for differentiating between survival of a porcine xenograft and a true zoonotic infection in a subject, comprising:

detecting the presence of a porcine endogenous retroviral nucleic acid in a sample from the subject; and detecting the presence of a porcine mitochondrial nucleic acid in the sample from the subject by a polymerase mediated technique that utilizes a nucleic acid having a sequence as set forth as SEQ ID NO: 1 or SEQ ID NO: 2;

wherein the comparable amounts of porcine endogenous retroviral nucleic acid and porcine mitochondrial nucleic acid indicate survival of the porcine xenograft and absence of a zoonotic infection.

15. The method of claim 14, wherein the detecting of porcine endogenous retroviral nucleic acid is by a polymerase mediated technique.

16. The method of claim 15, wherein the polymerase mediated technique utilizes a nucleic acid sequence comprising SEQ ID NO:6 or SEQ ID NO:7.

17. The method of claim 15, wherein the polymerase mediated technique is polymerase chain reaction.

18. The method of claim 14, wherein the porcine mitochondrial nucleic acid encodes a porcine cytochrome oxidase subunit II polypeptide.

19. The method of claim 1, wherein the polymerase mediated technique further comprises utilizing a nucleic acid probe having a sequence as set forth as SEQ ID NO:3.

20. The method of claim 8, wherein the polymerase mediated technique further comprises utilizing a nucleic acid probe having a sequence as set forth as SEQ ID NO:3.

21. The method of claim 14, wherein the polymerase mediated technique further comprises utilizing a nucleic acid probe having a sequence as set forth as SEQ ID NO:3.

22. The method of claim 9, wherein the polymerase mediated technique utilizes a nucleic acid having a sequence comprising SEQ ID NO:4 or SEQ ID NO:5.

23. The method of claim 15, wherein the polymerase mediated technique utilizes a nucleic acid sequence comprising SEQ ID NO:4 or SEQ ID NO:5.

* * * * *

SEQUENCE LISTING

<160> NUMBER OF SEQ ID NOS: 9

<210> SEQ ID NO 1
<211> LENGTH: 26
<212> TYPE: DNA
<213> ORGANISM: Porcine

<400> SEQUENCE: 1
tcacccatca tagaagaact cctaca                                    26

<210> SEQ ID NO 2
<211> LENGTH: 28
<212> TYPE: DNA
<213> ORGANISM: Porcine

<400> SEQUENCE: 2
ttttacggtt aaggctgggt tattaatt                                  28

<210> SEQ ID NO 3
<211> LENGTH: 24
<212> TYPE: DNA
<213> ORGANISM: Porcine

<400> SEQUENCE: 3
gacacacact agcacaatgg atgc                                      24

<210> SEQ ID NO 4
<211> LENGTH: 25
<212> TYPE: DNA
<213> ORGANISM: Porcine

<400> SEQUENCE: 4
ccacagggca acrrcagtat ccatg                                     25

<210> SEQ ID NO 5
<211> LENGTH: 24
<212> TYPE: DNA
<213> ORGANISM: Porcine

<400> SEQUENCE: 5
ttggagggtc aacacagtga tagg                                      24

<210> SEQ ID NO 6
<211> LENGTH: 27
<212> TYPE: DNA
<213> ORGANISM: Porcine

<400> SEQUENCE: 6
cggcaagaga agaatttgac taagatc                                   27

<210> SEQ ID NO 7
<211> LENGTH: 24
<212> TYPE: DNA
<213> ORGANISM: Porcine

<400> SEQUENCE: 7
cagttccttg cccagtgtcc tctt                                      24

<210> SEQ ID NO 8
<211> LENGTH: 24
<212> TYPE: DNA
<213> ORGANISM: Porcine

```
<400> SEQUENCE: 8
ccaagatggg agcwcaaatt tctt                                      24

<210> SEQ ID NO 9
<211> LENGTH: 24
<212> TYPE: DNA
<213> ORGANISM: Porcine

<400> SEQUENCE: 9
ggcaatagga ccccactcga caag                                      24
```